US007008416B2

(12) United States Patent  
Sakaguchi et al.

(10) Patent No.: US 7,008,416 B2  
(45) Date of Patent: Mar. 7, 2006

(54) MEDICAL ENERGY IRRADIATION APPARATUS

(75) Inventors: Akira Sakaguchi, Nakai-machi (JP); Wataru Karino, Nakai-machi (JP); Shin Maki, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 243 days.

(21) Appl. No.: 10/185,018

(22) Filed: Jul. 1, 2002

(65) Prior Publication Data

US 2003/0018325 A1 Jan. 23, 2003

(30) Foreign Application Priority Data

Jun. 29, 2001 (JP) ............................. 2001-199534

(51) Int. Cl.  
*A61B 18/00* (2006.01)

(52) U.S. Cl. ......................... 606/17; 606/14; 606/16; 600/108; 600/157

(58) Field of Classification Search ............... 600/157, 600/156, 108, 7, 13–18  
See application file for complete search history.

(56) References Cited

U.S. PATENT DOCUMENTS

| | | | |
|---|---|---|---|
| 4,211,229 A | 7/1980 | Wurster | |
| 4,445,892 A | 5/1984 | Hussein et al. | |
| 4,667,655 A | 5/1987 | Ogiu et al. | |
| 4,672,963 A | 6/1987 | Barken | |
| 4,760,840 A | 8/1988 | Fournier, Jr. et al. | |
| 4,773,413 A | 9/1988 | Hussein et al. | |
| 4,932,956 A | 6/1990 | Reddy et al. | |
| 4,932,958 A | 6/1990 | Reddy et al. | |
| 5,049,147 A | 9/1991 | Danon | |
| 5,167,220 A * | 12/1992 | Brown | 600/157 |
| 5,207,213 A * | 5/1993 | Auhll | 600/157 |
| 5,207,672 A | 5/1993 | Roth et al. | |
| 5,248,311 A | 9/1993 | Black et al. | |
| 5,292,320 A | 3/1994 | Brown et al. | |
| 5,350,375 A | 9/1994 | Deckelbaum et al. | |
| 5,450,846 A | 9/1995 | Goldreyer | |
| 5,464,008 A * | 11/1995 | Kim | 600/157 |
| 5,486,154 A * | 1/1996 | Kelleher | 600/104 |
| 5,496,308 A | 3/1996 | Brown et al. | |
| 5,769,843 A | 6/1998 | Abela et al. | |
| 6,117,071 A | 9/2000 | Ito et al. | |

(Continued)

FOREIGN PATENT DOCUMENTS

EP 0 673 627 A1 9/1995

(Continued)

*Primary Examiner*—David M. Shay  
(74) *Attorney, Agent, or Firm*—Buchanan Ingersoll PC

(57) ABSTRACT

To provide a medical energy irradiation apparatus which, having a simple and inexpensively manufacturable structure, enables a doctor using it in the heat curing of prostatic hypertrophy or the like to accurately and stably irradiate a prescribed site deep in a living body with a laser beam and, even if its observation window is smeared, to observe tissues of a living body. An inserting portion of the medical energy irradiation apparatus to be inserted into a living body according to the invention has an emitting portion for emitting a laser beam toward tissues of the living body; an observation window, provided near the tip of the inserting portion in its inserting direction, for observing the tissues of the living body; and a hollow pipe for supporting a supporting member, which supports the emitting portion, shiftably in the lengthwise directions of the inserting portion and feeding detergent to the observation window. Therefore, when the observation window is smeared, detergent can be fed to the observation window to remove the smear of the observation window.

13 Claims, 10 Drawing Sheets

U.S. PATENT DOCUMENTS

| | | |
|---|---|---|
| 6,171,303 B1 | 1/2001 | Ben-Haim et al. |
| 6,321,109 B1 | 11/2001 | Ben-Haim et al. |
| 6,379,347 B1 | 4/2002 | Maki et al. |
| 6,544,257 B1 * | 4/2003 | Nagase et al. ............ 606/15 |
| 2001/0053907 A1 | 12/2001 | Ota |
| 2002/0016619 A1 | 2/2002 | Iwahashi et al. |
| 2002/0022829 A1 | 2/2002 | Nagase et al. |
| 2002/0022869 A1 | 2/2002 | Hareyama et al. |
| 2002/0068963 A1 | 6/2002 | Maki et al. |

FOREIGN PATENT DOCUMENTS

| | | | |
|---|---|---|---|
| EP | 0 815 895 A1 | 1/1998 | |
| EP | 960601 | * 12/1999 | ............ 606/15 |
| EP | 1 075 822 A2 | 2/2001 | |
| JP | 2001-145630 A | 5/2001 | |
| WO | WO 92/04934 A1 | 4/1992 | |
| WO | WO 93/04727 A1 | 3/1993 | |
| WO | WO 00/74565 A1 | 12/2000 | |

\* cited by examiner

SECTIONAL STRUCTURE OF NON-PARALLEL GROOVES (POSITION B)

MEDICAL ENERGY IRRADIATION APPARATUS

BACKGROUND OF THE INVENTION

The present invention relates to a medical energy irradiation apparatus whose inserting portion is inserted into a living body cavity or tract such as a blood vessel, digestive tract, urinary tract, abdominal cavity or thoracic cavity, and the bodily tissue is irradiated with the energy of a laser beam, microwave, radio wave or ultrasonic wave from an emitting portion provided on this inserting portion to treat tissues of a body in morbidity, and more particularly to a cleaning method for observation windows in a medical energy irradiation apparatus for pinpoint heat curing of only a tumor, such as cancer, prostatic hypertrophy or the like, in a deep part of the body.

There are known energy irradiation apparatuses for medical use whose long inserting portion is inserted into a living body by utilizing an existing body cavity or incising a small hole to emit a laser beam, microwave, radio wave or ultrasonic wave to irradiate and treat tissues of a body in morbidity by eliminating the tissues in lesion by degeneration, necrosis, coagulation, cauterization or vaporization.

This kind of medical energy irradiation apparatus, which in its operation to cure the ailment usually directly irradiates with energy a lesion located on or near the surface layer of tissues of a living body, is also used for heat curing of a lesion located deep inside tissues of a living body such as the prostate gland. There is also known a medical energy irradiation apparatus of which the vicinities of the energy emitting portion provided on the inserting portion is cooled with coolant. Where this medical energy irradiation apparatus is used, since the energy emitting portion or the surface layer and its vicinities of tissues of a living body in contact with the vicinities of that portion are cooled, they are protected from heat injury, and a deeper part of tissues of the living body is heated concentratively.

For instance, in International Application Published under PCT No. WO9304727, a technique of coagulating and contracting part of tumorous or prostatic tissues by irradiation with a laser beam is disclosed. By this technique, heating of the surface of the urethra in contact with a balloon is avoided by injecting a coolant into the balloon, and instead only the tumor or prostate gland within is heated. However, as the laser beam is emitted from a fixed laser emitting portion, the irradiating laser output has to be low in order not to heat the urethra surface, inevitably resulting in the inconvenience of having to continue irradiation for a long period of time.

In U.S. Pat. No. 5,292,320, there is disclosed an apparatus for curing prostatic hypertrophy by guiding laser beams through the urethra. In this apparatus, laser beams emitted at the same time from a plurality of irradiating units arranged in different positions are concentrated on a deep lesional region, i.e. the target point of irradiation, to generate a sufficient calorific value for heating and contracting the tissue in the lesional region.

Therefore, although the temperature around the target point of irradiation is higher than in the regions where laser beams do not overlap each other, as the paths of the laser beams are fixed, a high-temperature region is formed even in the vicinity of the surface layer of the urethra, where laser beams do not overlap each other. This phenomenon adversely affects the protection of the surface layer of the urethra. Thus the inability of this apparatus to cure only a deep lesional region while reducing injuries to the surface layer poses a problem. Furthermore, since the plurality of irradiating units are contained, it is difficult to thin a main body.

Further, E.P. 1075822 discloses a laser beam irradiation apparatus for curing prostatic hypertrophy by guiding a laser beam through the urethra.

As this irradiation apparatus has a configuration in which its laser beam emitting portion continuously shifts to concentrate the laser beam from the emitting portion on the target point, the surrounding tissues other than the target point are kept at low temperature while the target point is heated to high temperature. For this reason, this laser beam irradiation apparatus is able to minimize, even when the target point is located in the depth of tissues of a living body, injuries to tissues of the living body positioned between the emitting portion and the target point, thereby capable of ensuring greater safety for the patient.

Incidentally, in trying to cure prostatic hypertrophy using the laser beam irradiation apparatus described above, the doctor would determine the target point for the laser beam in the following procedure, for instance.

The doctor inserts the inserting portion of the laser beam irradiation apparatus into the patient's urethra, fixes the laser beam emitting portion to match the position of the patient's urethra surrounded by the prostate while observing the urethra by way of an endoscope inserted into the inserting portion through an observation window installed on the inserting portion, and irradiates the lesion with a laser beam while aligning the emitting portion with the intended irradiating direction of the laser beam.

Thus the doctor inserts to a prescribed extent the inserting portion in which the endoscope is inserted into the patient's urethra toward the urinary bladder, and searches for the target point according to the shapes of different parts of the urethra observed through the endoscope in that position. If the target point is not found in the field of vision observable through the endoscope in that position, the doctor will repeat the above-described procedure until the target point is found by further inserting the inserting portion deeper into the patient's urethra to another prescribed extent toward the urinary bladder or otherwise.

The doctor will also repeat the above-described procedure on each target point in the heat curing with this laser beam irradiation apparatus if there are a plurality of target points to be irradiated with a laser beam.

Now, the above-described positioning of the laser beam target point may give rise to the following problem. Thus, when inserting the inserting portion through the patient's urethra toward the urinary bladder, if the observation window provided in the inserting portion is smeared by bleeding from the patient, for example, the field of vision through the observation window may be narrowed.

However, with the conventional laser beam irradiation apparatus described above (E.P. 1075822), once the observation window provided in the inserting portion is smeared, there is no other way to restore the full field of vision through the smeared observation window than to extract the inserting portion out of the patient's body and remove the contaminant on account of the absence of any mechanism for cleaning the observation window as shown in FIG. 8 and FIG. 9.

Also, the laser beam emitting portion according to EP 1075822 is small as shown in FIG. 8 and FIG. 10, and has a complex structure to keep the laser beam irradiation stably in a prescribed direction (toward the target point) all the time while continuously shifting the irradiating position of the laser beam. For this reason, it is difficult to secure a sufficient space in which is to be arranged a detergent feed pipe for cleaning the smeared observation window, when it is smeared as described above, in the inserting portion.

This difficulty to secure a sufficient space in which is to be arranged a mechanism for directing the laser beam stably toward a prescribed site all the time while continuously shifting the irradiating position of the laser beam and a detergent feed pipe in the inserting portion in the apparatus according to E.P. 1075822 will be described more specifically with reference to FIG. 8 through FIG. 10.

Laser reflecting means 1113 is fixed by a pair of arms 1116 fixed to the right and left sides of a supporting member 1114 fixed to the tip of an optical fiber 1108, and the pair of arms 1116 are slidably fitted by a pair of first stubs 1117 formed on the right and left sides of the laser reflecting means 1113 into a pair of rail grooves 1152 provided in a wall member 1151 provided within a housing 1102 (see FIG. 8). The rail grooves 1152 here are in parallel to the lengthwise direction of a body 1101.

A pair of second stubs 1118 formed on the right and left sides of the laser reflecting means 1113 are slidably fitted into a pair of rail grooves 1153 provided in the wall member 1151 within the housing 1102. The rail grooves 1153 here are not in parallel to the lengthwise direction of the body 1101.

Thus, the laser reflecting means 1113 shown in FIG. 10, with its structure using the pair of arms 1116, the pair of first stubs 1117, the pair of parallel rail grooves 1152, the pair of second stubs 1118 and the pair of non-parallel rail grooves 1153, can stably direct laser beam irradiation at the target point all the time while continuously shifting the irradiating position of the laser beam.

However, there is the need to provide the aforementioned arms and grooves within the housing 1102, resulting in a complex structure not allowing low-cost production. Also as stated above, because of the limited available space, when the observation window is smeared, it is difficult to secure a sufficient space for arranging a detergent feed pipe for cleaning the smeared observation window within the inserting portion.

SUMMARY OF THE INVENTION

The present invention, inspired by the perceived need to solve the above-described problems with the prior art, is intended to provide a medical energy irradiation apparatus which, in spite of its simple and inexpensively manufacturable structure, enables a doctor using it in heat curing of prostatic hypertrophy or the like to accurately and stably irradiate a prescribed site deep in a living body with a laser beam.

Another object of the invention is to provide a medical energy irradiation apparatus which enables a doctor using it in heat curing with the laser beam, even if its observation window is smeared, to readily remove the contaminant and to easily accomplish intended observation of tissues of a living body.

In order to attain the objects stated above, a medical energy irradiation apparatus in one aspect of implementing the invention has the following configuration. Thus, it is a medical energy irradiation apparatus having energy generating means for generating energy, the energy being emitted to irradiate tissues of a living body by an emitting portion provided within an inserting portion to be inserted into a living body, characterized in that the inserting portion has an observation window, provided the inserting portion, for observing the inside of a living body, and a hollow pipe for supporting the emitting portion, shiftably in the lengthwise directions of the inserting portion and feeding detergent to the observation window.

Here, it is preferable, for instance, for the inserting portion to have an irradiation window for irradiating the energy on a side of the inserting portion close to the observation window.

Here, it is preferable, for instance, for the medical energy irradiation apparatus further to have compressing means for compressing the detergent and feeding it through the hollow pipe to the observation window.

Here, it is preferable, for instance, for the detergent to be cleaning liquid or cleaning gas.

Here, it is preferable, for instance, for the cleaning liquid to be sterilized liquid.

Here, it is preferable, for instance, for the inserting portion to have one or more hollow pipes.

Here, it is preferable that, for instance, on the right and left walls of the inserting portion in its lengthwise direction, non-parallel rail grooves for defining the irradiating direction of the energy be provided.

Here, it is preferable, for instance, for the energy emitted from the emitting portion always to irradiate a prescribed site of the tissues of a living body irrespective of the position of the emitting portion.

Here, it is preferable, for instance, for the emitting portion, when reciprocating in the lengthwise directions of the inserting portion, to reflect the energy at an acute angle when the emitting portion is positioned toward the tip of the inserting portion and to reflect the energy at an obtuse angle when the emitting portion is positioned toward the basal end of the inserting portion.

Here, it is preferable, for instance, that the medium of the energy is a laser beam.

Other features and advantages of the present invention will be apparent from the following description taken in conjunction with the accompanying drawings, in which like reference characters denote the same or similar parts throughout the figures thereof.

BRIEF DESCRIPTION OF THE DRAWINGS

The accompanying drawings, which are incorporated in and constitute a part of the specification, illustrate an embodiment of the invention and, together with the description, serve to explain the principles of the invention.

DETAILED DESCRIPTION OF THE PREFERRED EMBODIMENTS

A preferred embodiment of the present invention will now be described in detail in accordance with the accompanying drawings.

Although the following description will concern a laser beam as an example of energy medium for use in the heat curing of prostatic hypertrophy or the like, the energy medium for use in heat curing need not be limited to a laser beam, but a microwave, radio wave or ultrasonic wave, for instance, can as well be used in place of a laser beam. Also, though the use of the medical energy irradiation apparatus according to the present embodiment for the heat curing of prostatic hypertrophy will be described as an example of its application, the application of the medical energy irradiation apparatus according to the present embodiment is not limited to the heat curing of prostatic hypertrophy, but can also be used for the heat curing of tumors such as cancer.

Figure 1:
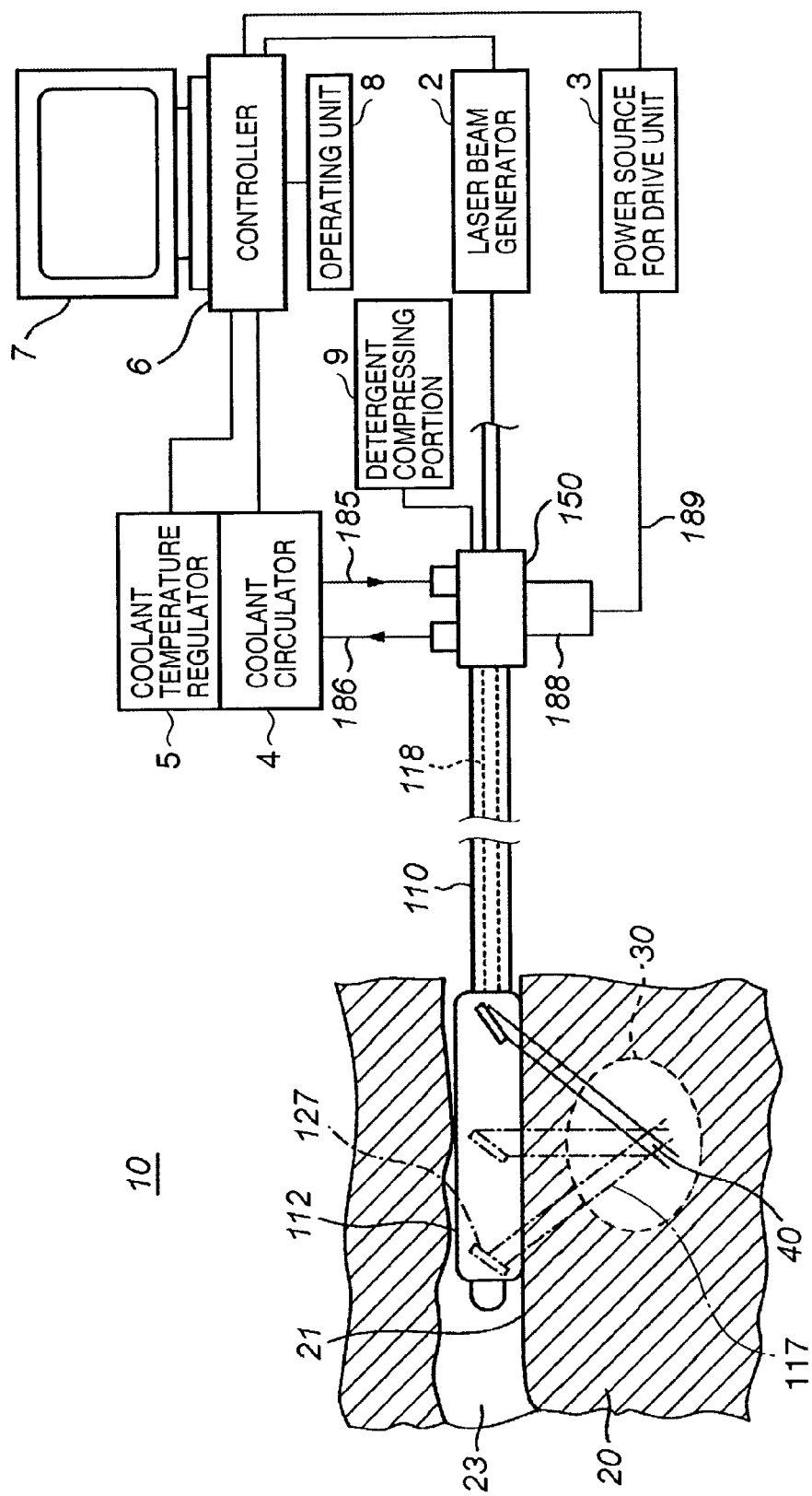
FIG. 1 shows a system configuration of a medical energy irradiation apparatus in one aspect of implementing the invention.

[Medical Energy Irradiation Apparatus: FIG. 1]

FIG. 1 shows the system configuration of a medical energy irradiation apparatus 10 in the present embodiment of the invention for use in the heat curing of prostatic hypertrophy.

This medical energy irradiation apparatus 10 has a side emitting type laser beam irradiating applicator 110 to be inserted into a living body (e.g. into a urethra 23). A laser beam 117 guided from a laser beam generator 2 via an optical fiber 118 is emitted from a housing 112 toward tissues of a living body 20.

The laser beam irradiating applicator 110 is further provided with a plurality of lumens (not shown) for coolant circulation communicating with the housing 112 arranged continuously in their tip vicinity, and these lumens are connected to a coolant feed tube 185 and a coolant return tube 186 of a coolant circulator 4.

The coolant circulator 4 feeds a set quantity of coolant to the laser beam irradiating applicator 110 in accordance with a control signal from a controller 6. A coolant temperature regulator 5 controls the temperature of the coolant by either heating or cooling it in accordance with a control signal from the controller 6. A motor 188 revolves at a set frequency in accordance with a control signal from the controller 6.

The controller 6 is provided with an operating unit 8 as input means, a display unit 7 for displaying input information and apparatus information, a control unit (not shown) for controlling different portions, a memory unit (not shown) for storing various information and an input/output unit (not shown) for various information.

During the heat curing of a target point 40 in the prostate gland with the laser beam, coolant is fed from the coolant circulator 4 to the laser beam irradiating applicator 110 via the coolant feed tube 185, the motor 188 revolves, and the laser beam generator 2 operates.

The generated laser beam 117 is guided to the tip of the laser beam irradiating applicator 110, reflected by a reflection plane 127 like a mirror, passes a window, and irradiates the target point 40 in the prostate gland. In this process, whereas the reflection plane 127 causes the angle of irradiation to vary while reciprocating in the axial directions in a cycle of 2 to 10 Hz, more preferably of 3 to 6 Hz, all the optical paths of the laser beam 117 cross at the target point 40 in the prostate gland (target tissue) 30, and accordingly the target point 40 in the prostate gland is continuously irradiated by the laser beam 117, resulting in the generation of a high calorific value and therefore high temperature.

On the other hand, on the surface layer 21 (i.e. the vicinity of the urethra surface) of the tissues of the living body 20, as the irradiating position of the laser beam 117 constantly shifts instead of being fixed at any single point, with its irradiating angle varied by the reciprocation of the reflection plane 127 in the axial direction, no great calorific value is generated and accordingly the position is kept at relatively low temperature, so that the surface layer 21 (the vicinity of the urethra surface) is protected from the effect of heating caused by the laser beam 117.

Figure 2:
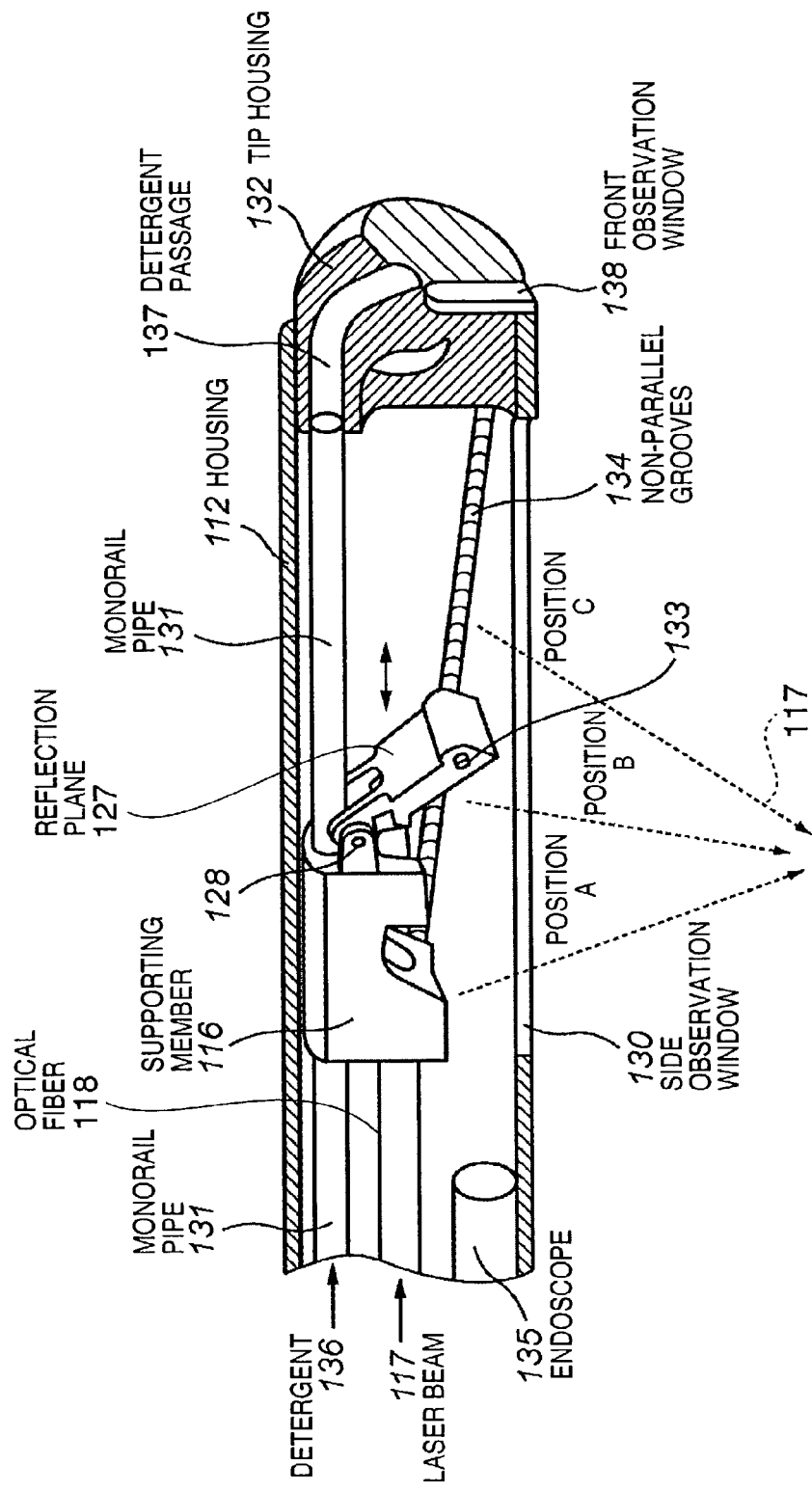
FIG. 2 illustrates a vicinity of a tip of an applicator in the aspect of implementing the invention.

[Applicator: FIG. 2]

FIG. 2 shows a perspective view of a section of the tip of the applicator 110.

First will be described the characteristics of the applicator 110 of the medical energy irradiation apparatus according to the present embodiment shown in FIG. 2.

1) The applicator 110 is provided with a mechanism for cleaning a front observation window 138 when the front observation window 138 for observing tissues of a living body is too much smeared to provide sufficient visibility through it. This mechanism is configured by a compressing portion 9 for feeding compressed detergent (liquid or gas) which is present at the basal end of the applicator 110, a hollow monorail pipe 131 for supplying the detergent fed from the compressing portion 9 to the front observation window 138 at the tip of the applicator 110, and a detergent passage 137 provided in a tip housing 132. As the detergent passes through the hollow monorail pipe 131 and is ejected near the front observation window 138, any smear on the front observation window 138 is removed. As the compressing portion 9 for compressing and feeding the detergent, a known compressive feeding apparatus for pressure feeding of liquid or gas can be used.

2) An emitting portion of the laser beam comprises the reflection plane 127 and a supporting member 116. The monorail pipe 131 is arranged parallel to the lengthwide direction of the applicator 110 and has, in addition to the aforementioned detergent feeding function, the function of an axis to hold the supporting member 116 for supporting the reflection plane 127 which reflects the laser beam and enable it to reciprocate in the lengthwise directions of the applicator 110. The supporting member 116 varies the irradiating position of the laser beam by reciprocating on the monorail pipe 131. The reflection plane 127 is slidably fitted into non-parallel grooves 134 which are not parallel to the monorail pipe 131. This simple structure having these features allows the irradiating direction of the laser beam to be stably directed all the time at the target point while varying the irradiating position.

The applicator 110 of the medical energy irradiation apparatus according to the present embodiment, by virtue of its features stated in 1) and 2), can be manufactured in a simpler structure than according to the prior art and, moreover, permits removal of any smear left on the front observation window by bleeding from the patient or otherwise without having to provide an additional space for feeding detergent.

The tip of the applicator 110 will be described below.

As shown in FIG. 2, the applicator 110 is provided with the tip housing 132 having the front observation window 138, the smooth reflection plane 127 contained in the housing 112 and reflecting the laser beam 117, the supporting member 116 for supporting the reflection plane 127, the monorail pipe 131 for enabling the supporting member 116 to reciprocate in the lengthwise directions of the applicator 110, the non-parallel grooves 134 for varying the angle of the reflection plane 127 so that the laser beam 117 reflected by the reflection plane 127 be emitted in the same direction all the time, and an endoscope 135 for observing tissues of a living body.

Here, the reflection plane 127 is rotatably supported by a pair of arms 128 fixed to the right and left sides of the supporting member 116 fixed to the tip of the optical fiber 118. A pair of stubs 133 formed on the right and left sides of the reflection plane 127 are slidably fitted into the pair of non-parallel grooves 134 provided in a wall member within the housing 112. The non-parallel grooves 134 are not parallel to the lengthwise direction of the applicator 110.

The above-described structure enables the emission of the laser beam to be emitted in a prescribed direction (toward the target point) all the time when the supporting member 116 reciprocates on the monorail pipe 131 in the directions of arrows in FIG. 2, i.e. in the lengthwise directions of the applicator 110 (e.g. position A→position B→position C→position B→position A or the like). For this reason, the irradiating position and the irradiating direction of the laser beam 117 can be so controlled as to continuously vary all the time, so that the laser beam 117 never be fixed in the same direction when it is emitted.

The monorail pipe 131 described above has not only the role of enabling the supporting member 116 to reciprocate in the lengthwise directions of the applicator 110 but also the role of piping which, when the front observation window 138 of the tip housing 132 has been smeared, channels detergent (e.g. cleaning liquid or gas) supplied from the compressing portion 9 (cleaning unit) to the front observation window 138.

Thus, the monorail pipe 131 is hollow as shown in FIG. 2, and therefore can let detergent, such as cleaning liquid or gas pass within it. The cleaning liquid usable here may be, for instance, sterilized water or sterilized saline.

The cleaning liquid is fed in a compressed state from the compressing portion 9 (cleaning unit) to the inside of the monorail pipe 131 so that any contaminant sticking to the front observation window 138 can be readily removed. It is fed to the front observation window 138 via the detergent passage 137 of the tip housing 132, and removes any contaminant sticking to the front observation window 138.

Where cleaning gas is to be used instead of cleaning liquid, compressed air, nitrogen or oxygen gas can be chosen for the purpose.

The reflection plane 127 is linked via the supporting member 116 and the optical fiber 118 reinforced by a metal pipe or the like to a drive unit 150 (see FIG. 1) arranged at the basal end of the applicator 110, and shifting of the supporting member 116 in the lengthwise directions of the applicator 110 enables the reflection plane 127 to reciprocate in the directions indicated by arrows in the figure.

The drive unit 150 (FIG. 1) has a cam mechanism (not shown) for converting the revolution of the motor 188 (FIG. 1) into reciprocation, and the revolution of the motor 188 (FIG. 1) causes the reflection plane 127 to reciprocate in the lengthwise directions of the applicator 110. The housing 112 consists of a hard tubular body having a side observation window 130 through which the laser beam 117 is to be emitted.

Figure 3:
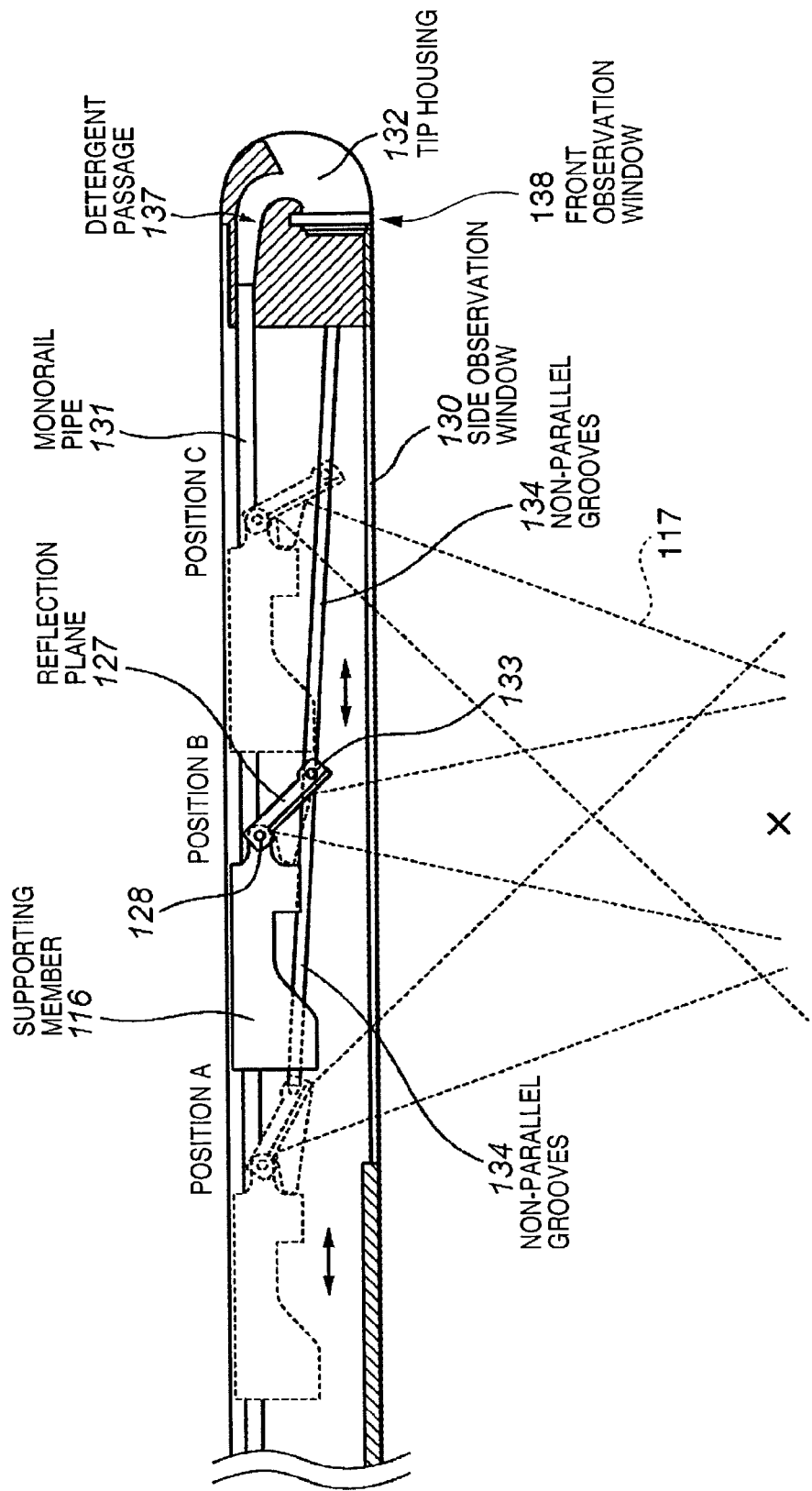
FIG. 3 illustrates a relationship between an action of a reflection plane of the applicator and an irradiating direction of a laser beam in the aspect of implementing the invention.

[Structure of Reflection Plane and Supporting Member: FIG. 3]

FIG. 3 is a sectional view showing the reflection plane 127 and the supporting member 116 sliding on the monorail pipe 131 of the applicator 110 described with reference to FIG. 2.

The supporting member 116 supports the reflection plane 127. On one side of the reflection plane 127 is provided a support 128 and on another side of it are arranged the pair of stubs 133. The support 128 is fitted to enable the reflection plane 127 to freely rotate, against with the supporting member 116, and is adaptable to changes in the reflection angle of the reflection plane 127. Stubs 133 are fitted into the non-parallel grooves 134 arranged in the inner wall of the housing 112.

The supporting member 116 is linked to the drive unit 150 (FIG. 1) arranged at the basal end of the applicator 110 via the optical fiber 118 whose diagram is omitted in FIG. 3 in order to explain the movement of the emitting portion, and causes the reflection plane 127 to reciprocate in the lengthwise directions of the applicator 110 by sliding on the monorail pipe 131. For this reason, the reflection plane 127 can vary the angle of inclination along with shifting in the axial direction on the basis of interlocking between the supporting member 116 and the non-parallel grooves 134.

Figure 4:
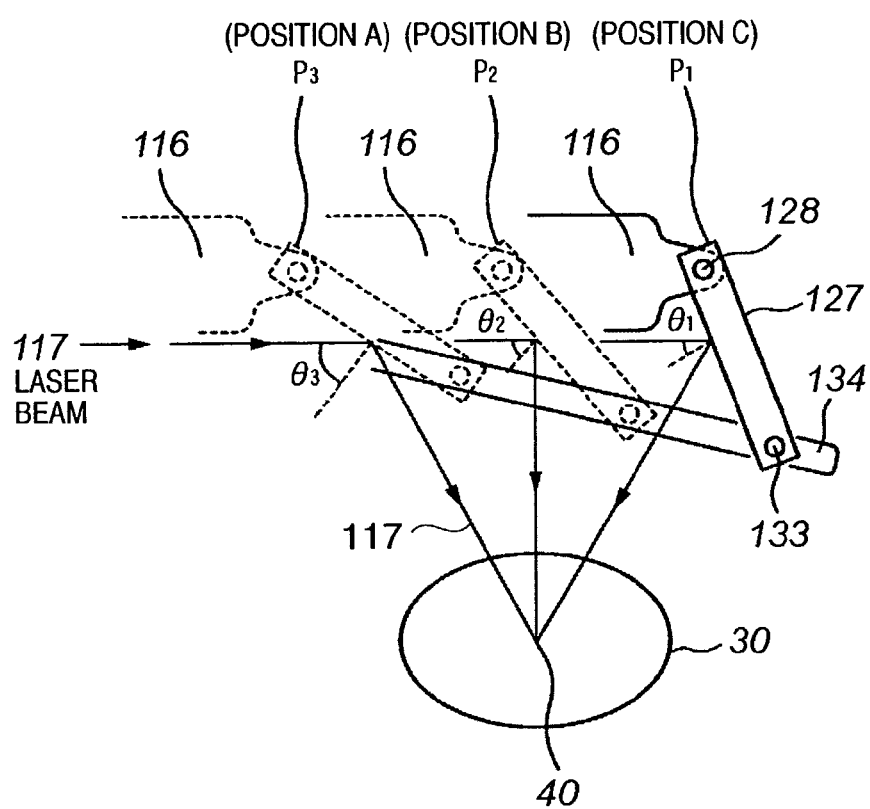
FIG. 4 illustrates a relationship between the action of the reflection plane and positions of a target point on tissues of a living body on which the laser beam is concentrated in the aspect of implementing the invention.

[Relationship Between Reflection Plane and Laser Beam: FIG. 4]

FIG. 4 illustrates the relationship between the motion of the reflection plane 127 and the irradiating direction of the laser beam 117.

As shown in FIG. 4, the distance between the supporting member 116 and the non-parallel grooves 134 at $P_2$ (position B) is shorter than that at $P_1$ (position C). For this reason, when the support 128 of the reflection plane 127 shifts from $P_1$ (position C) to $P_2$ (position B), the stubs 133 of the reflection plane 127 slide along the non-parallel grooves 134, and the angle of inclination of the reflection plane 127 is thereby regulated. Thus, the angle of inclination of the reflection plane 127 relative to the monorail pipe 131 is regulated to become narrower.

Similarly, when the support 128 of the reflection plane 127 shifts from $P_2$ (position B) to $P_3$ (position A), the inclination angle of the reflection plane 127 relative to the monorail pipe 131 is regulated to become even narrower.

On the other hand, at $P_1$ (position C) through $P_3$ (position A), the laser beam 117 reflected by the reflection plane 127 is set to concentrate all the time on the target point 40 of the targeted prostate gland (target tissue) 30. For this reason, the laser beam 117 irradiates only the target point 40 continuously and other tissues including the surface layer intermittently. Therefore, the target point 40 which is continuously irradiated with the laser beam 117 is heated and reaches a desired high temperature because the calorific value generated there is increased by the irradiation. On the other hand, other sites than the target point 40 such as the surface layer 21, which are intermittently irradiated with the laser beam 117, are not heated significantly because the calorific value generated there is small. Therefore, only the target point 40 and its vicinities can be heated by the laser beam 117 to reach the desired high temperature while restraining the temperature rise in the surface layer 21 area.

Incidentally, though the non-parallel grooves 134 were assumed to be linear in the foregoing description, their shape need not be always linear, but can be curved as well.

The reflection plane 127 which reflects the laser beam 117 reciprocates in the lengthwise directions of the applicator 110 in a cycle of 2 to 10 Hz, more preferably of 3 to 6 Hz, on the monorail pipe 131 while varying its angle.

It is desirable for the laser beam 117 emitted here to be divergent, collimate or convergent. An optical system for converging the laser beam 117 may as well be provided midway on the optical path of the laser beam 117. The laser beam 117 to be used is confined to no particular type if only it has penetrate in a living body, though its preferable wavelength range is 750 to 1300 nm or 1600 to 1800 nm.

For instance, a gaseous laser such as He—Ne laser, a solid laser such as Nd-YAG laser or a semiconductor laser such as GaAlAs laser can be applied to the laser beam generator 2 for generating the laser beam 117 of either of the aforementioned wavelength ranges. The diameter of the inserting portion of the applicator 110, i.e. the outside diameter of the applicator 110, has no particular limitation if only the applicator 110 can be inserted into a body cavity 22. However, it is preferable for the outside diameter of the applicator 110 to be between 2 and 20 mm, more preferably between 3 and 8 mm.

Figure 5:
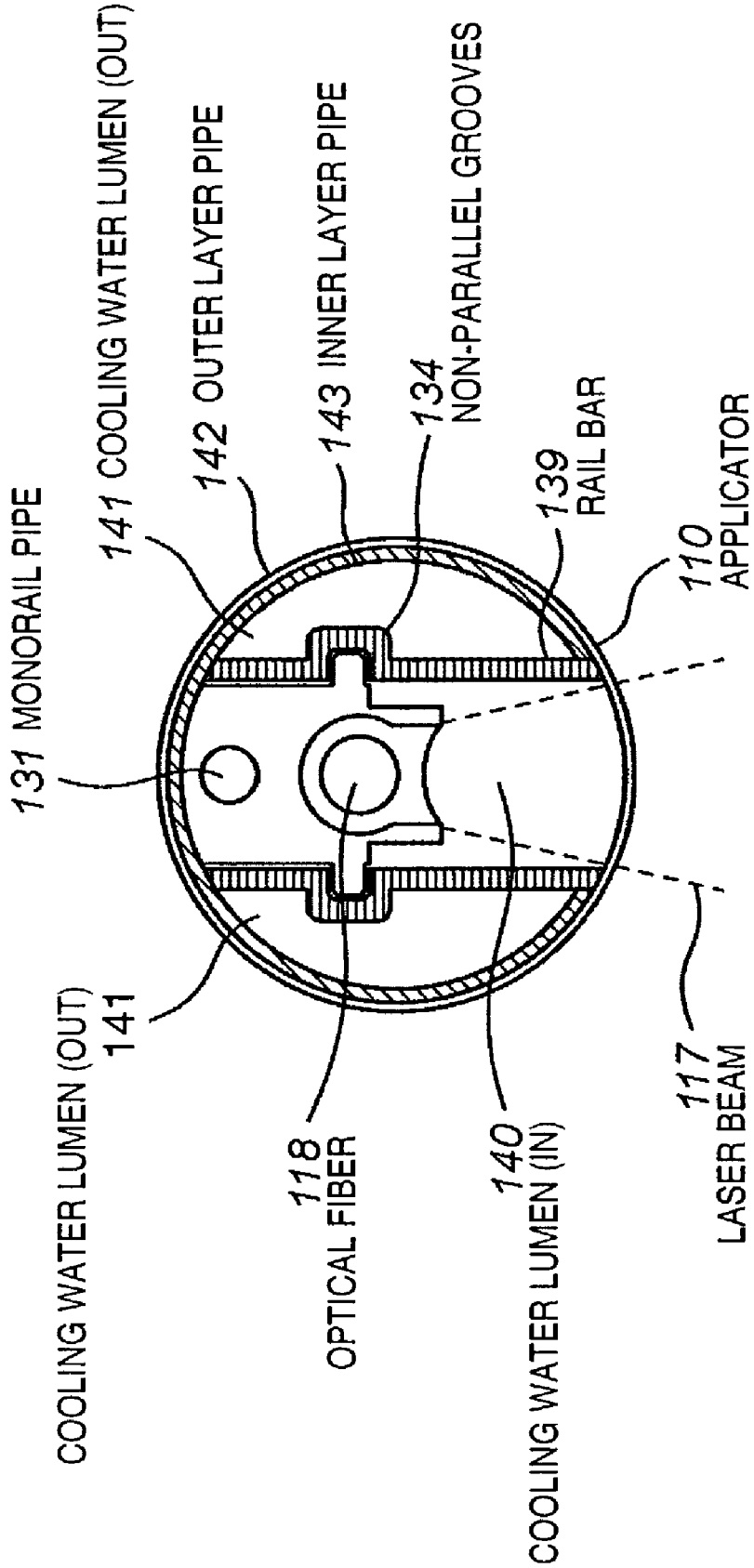
FIG. 5 illustrates an example of sectional structure (in position A) of non-parallel grooves in the aspect of implementing the invention.
Figure 6:
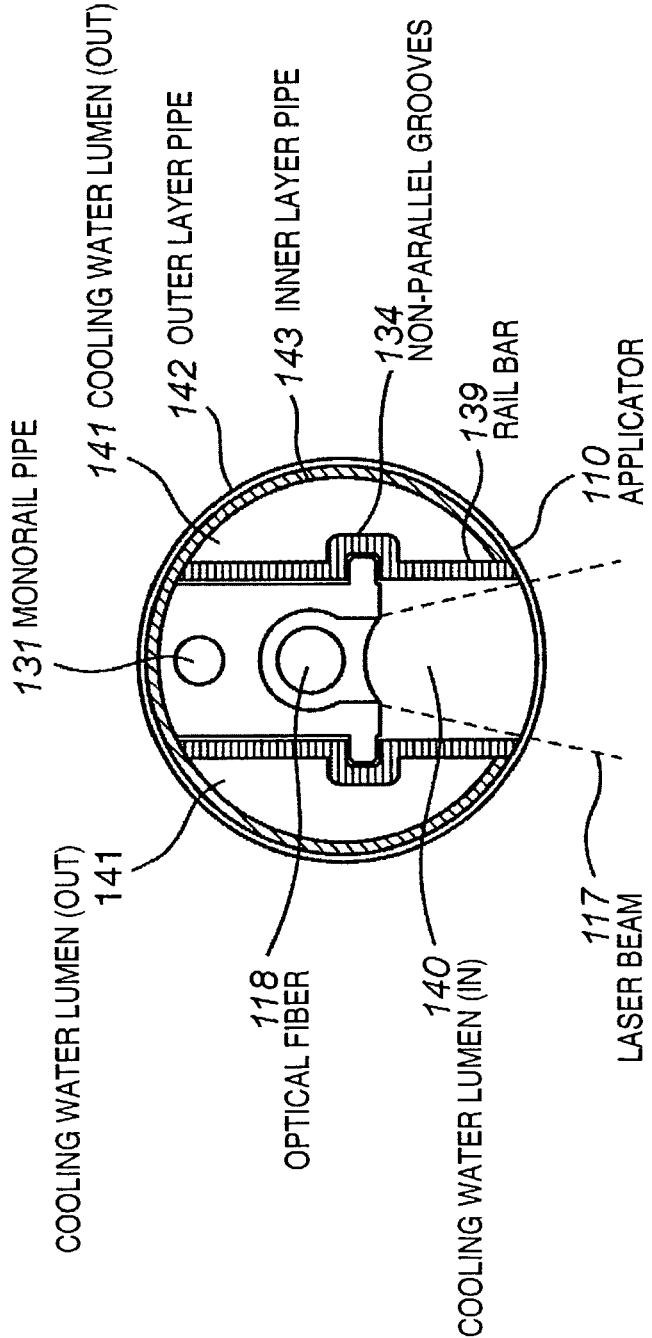
FIG. 6 illustrates an example of sectional structure (in position B) of non-parallel grooves in the aspect of implementing the invention.
Figure 7:
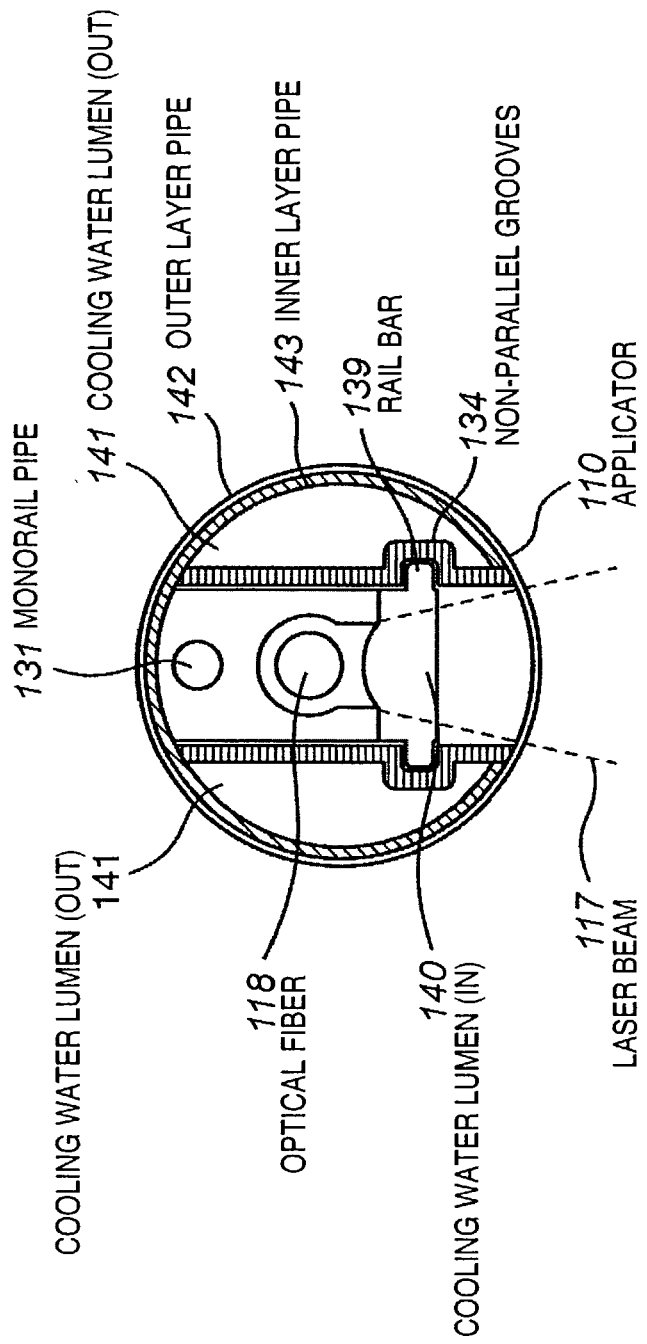
FIG. 7 illustrates an example of sectional structure (in position C) of non-parallel grooves in the aspect of implementing the invention.
Figure 8:
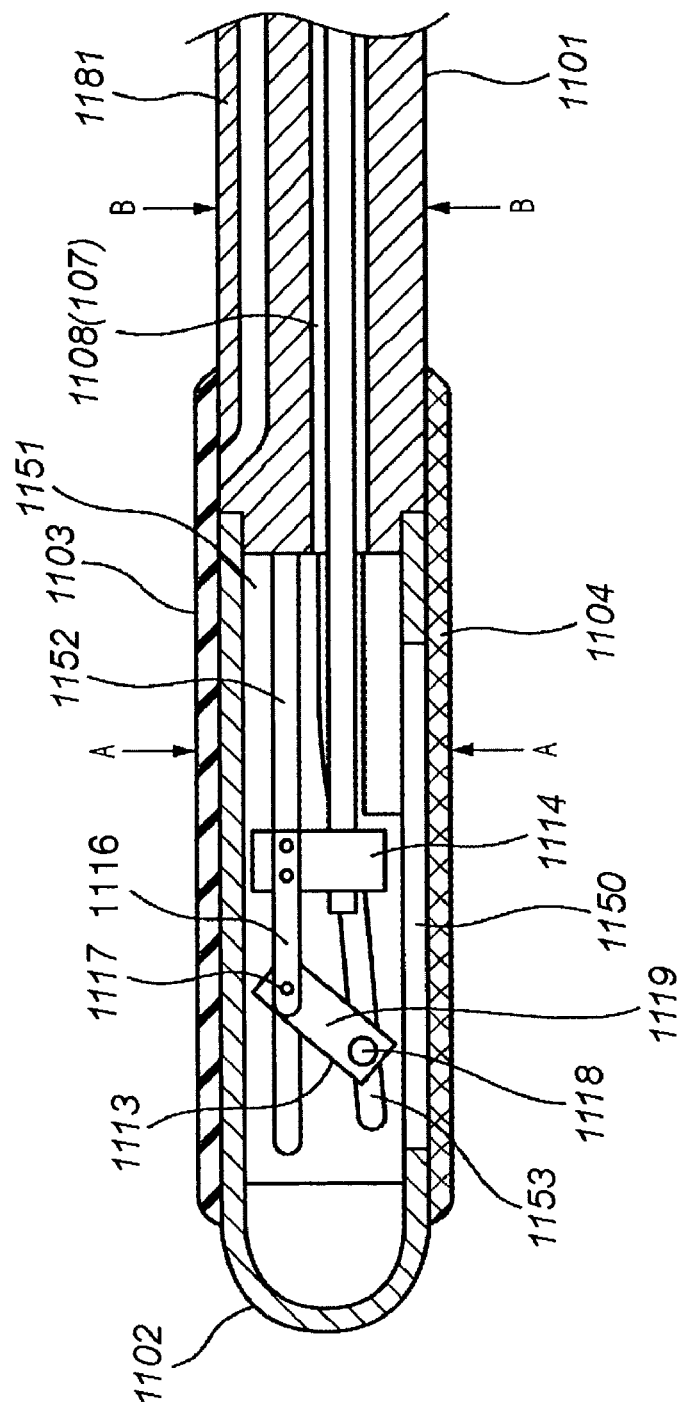
FIG. 8 shows a lateral section of a tip structure of an inserting portion of a medical energy irradiation apparatus according to the prior art.
Figure 9:
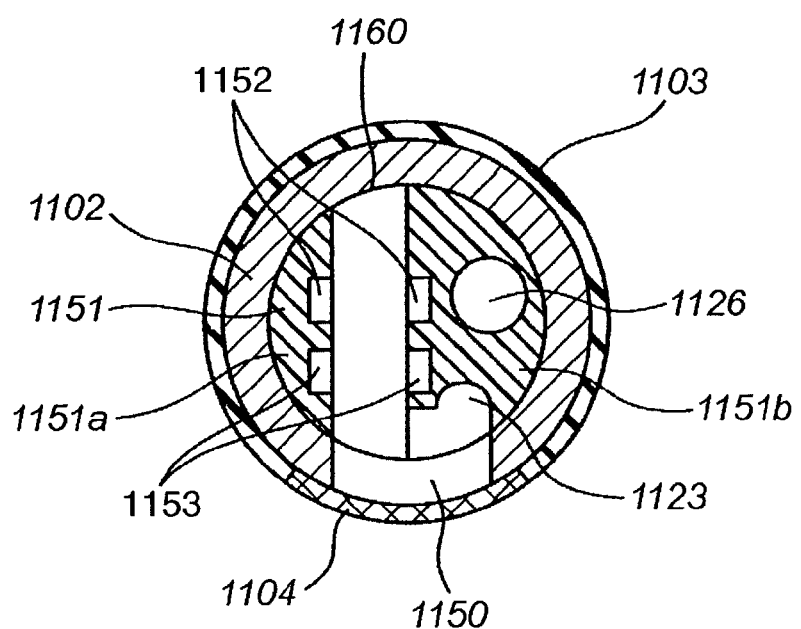
FIG. 9 shows a section of the tip structure of the inserting portion of the medical energy irradiation apparatus according to the prior art.
Figure 10:
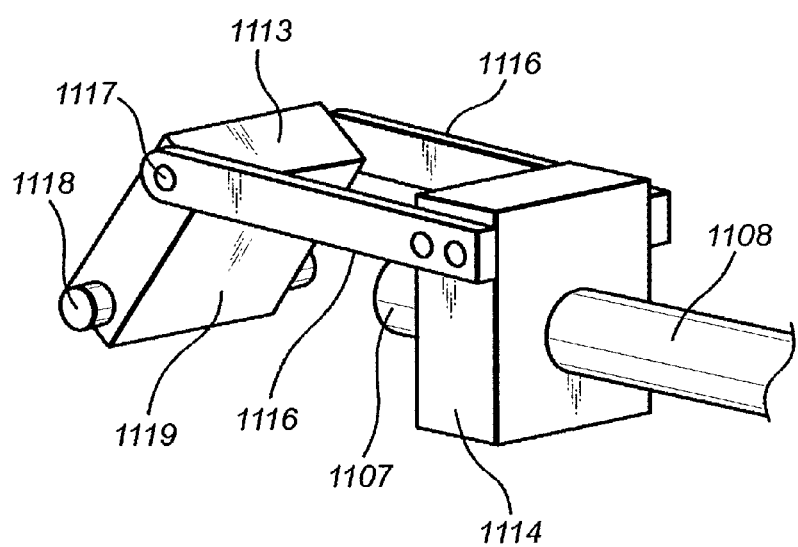
FIG. 10 illustrates a structure of laser beam reflecting means of the medical energy irradiation apparatus according to the prior art.

[Non-parallel Grooves: FIG. 5 through FIG. 7]

Next will be further explained the structure of the non-parallel grooves 134 described above with reference to sectional structural diagrams of FIG. 5 through FIG. 7.

FIG. 5 through FIG. 7 show sections of the applicator 110 in positions A, B and C in FIG. 3, illustrating differences in the position of the non-parallel grooves 134 provided in rail bars 139 from one position to another.

In FIG. 5 through FIG. 7, in the central part of the applicator 110 are arranged the two rail bars 139, and between the two rail bars 139 are disposed the monorail pipe 131 for carrying the detergent, a fiber 118 for guiding the laser beam and a cooling water lumen (in) 140 for feeding cooling water to the tip of the applicator 110.

At the left or right end of each of the rail bars 139 and the applicator 110 are arranged a cooling water lumen (out) 141 for returning to the coolant circulator 4 the cooling water fed to the tip of the applicator 110, an outer layer tube 142 and an inner layer pipe 143.

The position of the non-parallel grooves 134 in position A in FIG. 5 is higher than the position of the non-parallel grooves 134 in position B in FIG. 6. For this reason, the reflection angle $\theta_3$ of the reflection plane 127 reflecting the laser beam 117 in position A shown in FIG. 4 is greater than the reflection angle $\theta_2$ in position B shown in FIG. 4.

Similarly, the position of the non-parallel grooves 134 in position B in FIG. 6 is higher than the position of the non-parallel grooves 134 in position C in FIG. 7. For this reason, the reflection angle $\theta_2$ of the reflection plane 127 reflecting the laser beam 117 in position B shown in FIG. 4 is greater than the reflection angle $\theta_1$ in position C shown in FIG. 4.

Therefore, the laser beam 117 reflected by the reflection plane 127 can always be focused on the target site 40 by utilizing the positional difference of the non-parallel grooves 134.

The embodiment so far described is not intended to limit the present invention, but can be altered in various ways within the scope of the technical idea of the invention. Although a laser beam was taken up as an example of energy medium to irradiate tissues of a living body, the invention is not limited to this, but can as well use some other energy medium, such as a microwave, radio wave or ultrasonic wave. It is desirable for the medical energy irradiation apparatus according to the invention to be applied to the heat curing of only the prostate gland in, for instance, treating a prostate gland disease such as prostatic hypertrophy or prostate gland cancer, while alleviating heat-induced injuries to healthy tissues present in the vicinities of the prostate gland including the urethra and rectum. Furthermore, the monorail pipe may comprise a plurality of pipes.

As hitherto described, according to the invention, there is provided a medical energy irradiation apparatus which, in spite of its simple and inexpensively manufacturable structure, enables a doctor using it in heat curing of prostatic hypertrophy or the like to accurately and stably irradiate a prescribed site with a laser beam. The invention can also provide a medical energy irradiation apparatus which enables a doctor using it in heat curing, even if its observation window is smeared, to readily accomplish intended observation of tissues of a living body.

As many apparently widely different embodiments of the present invention can be made without departing from the spirit and scope thereof, it is to be understood that the invention is not limited to the specific embodiment thereof except as defined in the claims.

What is claimed is:

1. A medical energy irradiation apparatus having energy generating means for generating energy, in which said energy is emitted to irradiate tissues of a living body by an emitting portion provided within an inserting portion to be inserted into a living body, said inserting portion comprising:

a front observation window, provided adjacent a front tip of said inserting portion, for observing an inside of a living body, a side window through which the energy is emitted, said side window situated rearwardly of the front observation window, and a hollow pipe defining an axis extending in a lengthwise direction of said inserting portion, said hollow pipe supporting said emitting portion for movement along said axis relative to said hollow pipe, said hollow pipe arranged to feed detergent to said front observation window.

2. The medical energy irradiation apparatus, according to claim 1, further comprising compressing means for compressing said detergent and feeding the detergent through said hollow pipe to said observation window.

3. The medical energy irradiation apparatus according to claim 1, wherein said inserting portion has a plurality of hollow pipes.

4. The medical energy irradiation apparatus according to claim 1, wherein, on right and left walls of said inserting portion in its lengthwise direction, non-parallel grooves for defining the irradiating direction of said energy are provided.

5. The medical energy irradiation apparatus according to claim 1, wherein said energy is a laser beam.

6. The medical energy irradiation apparatus according to claim 1, wherein said detergent is cleaning liquid or cleaning gas.

7. The medical energy irradiation apparatus according to claim 6, wherein said cleaning liquid is sterilized liquid.

8. The medical energy irradiation apparatus according to claim 1, wherein said energy emitted from said emitting portion always irradiates a prescribed site of said tissues of a living body irrespective of the position of said emitting portion.

9. The medical energy irradiation apparatus according to claim 8, wherein said emitting portion, when reciprocating in lengthwise directions of said inserting portion, reflects said energy at an acute angle when said emitting portion is positioned toward a tip of said inserting portion and reflects said energy at an obtuse angle when said emitting portion is positioned toward a basal end of said inserting portion.

10. The medical energy irradiation apparatus according to claim 1, wherein said emitting portion comprises a reflection plane which is supported by a tip of an optical fiber.

11. The medical energy irradiation apparatus according to claim 10, wherein a reflecting angle of the reflection plane is changed as the reflection plane reciprocates on said hollow pipe.

12. The medical energy irradiation apparatus according to claim 1, wherein said emitting portion comprises a supporting member which is slidable along at least a portion of an outer periphery of the hollow pipe.

13. The medical energy irradiation apparatus according to claim 12, wherein said emitting portion also comprises a reflection plane rotatably supported on the supporting member so that the reflection plane and the supporting member are slidable together along at least a portion of the hollow pipe.

* * * * *